United States Patent [19]

Ohnishi et al.

[11] Patent Number: 4,659,510

[45] Date of Patent: Apr. 21, 1987

[54] TRIMETHYLCYCLOHEXENYL COMPOUNDS AND AROMA COMPOSITIONS CONTAINING THE SAME

[75] Inventors: Takashi Ohnishi; Shigeaki Suzuki; Yoshiji Fujita; Takashi Nishida, all of Kurashiki, Japan

[73] Assignee: Kuraray Company, Ltd., Kurashiki, Japan

[21] Appl. No.: 671,194

[22] Filed: Nov. 14, 1984

[51] Int. Cl.$^4$ .................. A61K 7/46; C07C 49/21
[52] U.S. Cl. .................. 252/522 R; 568/378; 568/377; 426/650
[58] Field of Search .................. 568/377, 378; 252/522 R

[56] References Cited

U.S. PATENT DOCUMENTS

| | | | |
|---|---|---|---|
| 3,822,315 | 7/1974 | Klein | 568/377 |
| 3,968,161 | 7/1976 | Schults-Elte | 568/377 |
| 3,975,310 | 8/1976 | Kovats et al. | 568/377 |
| 4,174,284 | 11/1979 | Moakherjee et al. | 568/378 |
| 4,292,447 | 9/1981 | Trenkle et al. | 568/378 |

FOREIGN PATENT DOCUMENTS 8403508  9/1984  European Pat. Off. ............ 568/377

Primary Examiner—James H. Reamer
Attorney, Agent, or Firm—Oblon, Fisher, Spivak, McClelland & Maier

[57] ABSTRACT

Novel trimethylcyclohexenyl compounds of the 1,3,3-trimethyl-1-cyclohexene type having a 3-hydroxy-3-lower alkylpropionyl group at the 6-position of the cyclohexene are provided. These trimethylcyclohexenyl compounds have a floral note reminiscent of a variety of odors. There are also provided aroma compositions containing these compounds.

9 Claims, No Drawings

TRIMETHYLCYCLOHEXENYL COMPOUNDS AND AROMA COMPOSITIONS CONTAINING THE SAME

BACKGROUND OF THE INVENTION

1. Field of the Invention

This invention relates to trimethylcyclohexenyl compounds of the 1,3,3-trimethylcyclohexene type having a 3-hydroxy-3-lower alkylpropionyl group at the 6-position of the cyclohexene and aroma compositions containing the same.

2. Description of the Prior Art

It is known that cycloaliphatic crotonoyl compounds such as 2,4,4-trimethyl-1-trans-crotonoyl-2-cyclohexene bear and yield a natural fruity odor and increase wine-like and fresh flower-like nuances (cf. U.S. Pat. No. 3,822,315).

It is also known that 2,6,6-trimethyl-1-crotonoyl-1-cyclohexene, 2,6,6-trimethyl-1-crotonoyl-2-cyclohexene and the like have fruity, herb-like, winy, woody, floral or waxy flavor notes and, in some instances, impart a red berry-like flavor to products, and further enhance the taste and flavor of such products as honey and wine (cf. U.S. Pat. No. 3,928,456).

An object of the present invention is to provide novel trimethylcyclohexenyl compounds that are particular and different in odor from known cyclohexenyl compounds such as mentioned above.

Another object of the invention is to provide the use of said novel trimethylcyclohexenyl compounds having particular odor as ingredients of compounded perfumes or food flavoring agents.

These objects as well as other objects and advantages of the invention will become apparent to those skilled in the art from the following detailed description.

SUMMARY OF THE INVENTION

In accordance with the present invention, there are provided trimethylcylohexenyl compounds of general formula (I)

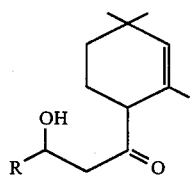

(I)

wherein R is a lower alkyl group.

The invention also provides aroma compositions containing a trimethylcyclohexenyl compound of the above formula (I).

DETAILED DESCRIPTION OF THE INVENTION

In the above formula, R is a lower alkyl group such as methyl, ethyl, propyl or butyl. As will be described later herein, a methyl group is a particularly preferred species of R from the viewpoint of odoriferous characteristics owned by the trimethylcyclohexenyl compounds of general formula (I).

The present inventors synthesized a large number of cyclohexenyl compounds and investigated their characteristics as aroma chemicals and, as a result, found that trimethylcyclohexenyl compounds represented by the above general formula (I) are odoriferous compounds which have a slight camphor-like odor and floral odor with a sweet fruity note and are reminiscent of a cedar- or ionone-like woody note as well as a warm tabac note and a musk- or ambergris-like animal note and that said compounds are satisfactory from both the diffusion and retention viewpoints and have favorable properties rendering them compatible with a variety of fragrance materials.

The trimethylcyclohexenyl compounds of general formula (I) are superior in diffusion and retention to the prior art cyclohexenyl compounds as mentioned above.

The trimethylcyclohexenyl compounds according to the invention can be added to perfume, fragrance compositions in their pure forms or they can be added to mixtures of materials in fragrance-imparting compositions to provide a desired fragrance character to a finished perfume material. The perfume, fragrance compositions obtained according to the invention are suitble in a wide variety of perfumed articles and can also be used to enhance, modify or reinforce natural fragrance materials. It will thus be appreciated that the trimethylcyclohexenyl compounds according to the invention each are useful as olfactory agents and fragrances.

The term "perfume, fragrance composition" is used herein to mean a mixture of compounds, including, for example, natural oils, synthetic oils, alcohols, aldehydes, ketones, esters, lactones, and frequently hydrocarbons which are admixed so that the combined odors of the individual components produce a pleasant or desired fragrance. Such perfume, fragrance compositions usually contain (a) the main note or the bouquet or foundation-stone of the composition, (b) modifiers which round off and accompany the main note, (c) fixatives which include odorous substances which lend a particular note to the composition throughout all stages of evaporation, and substances which retard evaporation, and (d) top notes which are usually low-boiling fresh-smelling materials. Such perfume, fragrance compositions of the invention can be used in conjunction with carriers, vehicles, solvents, dispersants, emulsifiers, surface-active agents, aerosol propellants and the like.

In perfume, fragrance compositions, the individual components contribute their particular olfactory characteristics, but the overall effect of the perfume, fragrance composition will be the sum of the effect of each ingredient. Thus, the trimethylcyclohexenyl compounds according to the invention can be used alone or in combination to alter the aroma characteristics of a perfume, fragrance composition, for example, by highlighting or moderating the olfactory reaction contributed by another ingredient of the composition.

The perfume, fragrance composition according to the invention contains an olfactorily sensible amount of the trimethylcyclohexenyl compounds as represented by general formula (I). The proportion of the trimethylcyclohexenyl compounds as represented by general formula (I) in the total composition may vary according to the intended use of the composition; for example, it may range from about 0.005 weight percent to 95 weight percent. The perfume, fragrance composition of the invention can be used in a large variety of ways. For example, it can be used as or in soaps; space deodorants; perfumes and eau de cologne; cosmetic preparations such as lotions, creams, etc.; bath supplies such as bath oil, bath salts, etc.; hair preparations such as hair tonics, pomades, hair liquids, hair creams, stick pomades, shampoos, rinses, etc.; cleansers; detergents, etc. In addition, the perfume, fragrance composition can also be used for scenting such substrates as textile fibers and fabrics, paper products and so on.

Compare further our pending Japanese Patent Application No. 83653/82, filed on May 17, 1982, published on Nov. 24, 1983, hereby expressly incorporated by reference and relied upon.

The trimethylcyclohexenyl compounds according to the invention are also useful as ingredients for the preparation of artificial flavors and as flavor additives in foodstuffs, animal feeds, beverages, pharmaceutical preparations and tobacco products. The term "foodstuff" is used in this specification in its broadest sense and is meant to include also products such as coffee, tea and cocoa.

When the trimethylcyclohexenyl compounds according to the invention are used as flavoring agents or additives for modifying the organoleptic properties of foodstuffs, animal feeds, beverages, pharmaceutical preparations and tobacco products, said trimethylcyclohexenyl compounds can be used in proportions which, again, vary within wide limits. Interesting flavoring effects, for instance, can be achieved by using the trimethylcyclohexenyl compounds according to the invention in proportions from 0.1 to 10 ppm based on the weight of the products to be flavored. However, these proportions can be increased beyond 10 ppm up to about 100 ppm in order to achieve special flavoring effects. In the preparation of flavoring compositions by admixing the trimethylcyclohexenyl compounds to other aromatics, the said compounds can be used, for example, in proportions of about 0.1% to about 15% of the total weight of the flavoring composition. In many cases average proportions of about 1 to 10% by weight will give the desired results.

The trimethylcyclohexenyl compounds of general formula (I) can be produced easily, for example, via the route given below starting with the per se known 1-acetyl-2,4,4-trimethyl-2-cyclohexene.

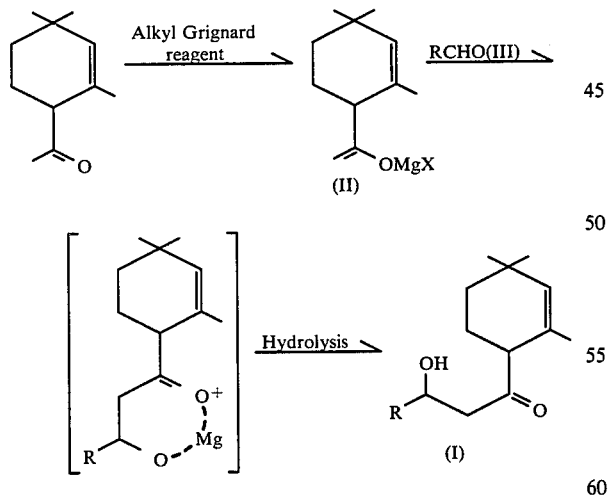

In the above formulas, X is a halogen atom and R is as defined above relative to general formula (I).

Thus, 1-acetyl-2,4,4-trimethyl-2-cyclohexene and an alkyl Grignard reagent such as ethylmagnesium chloride, ethylmagnesium bromide, etc. are reacted in a solvent such as diethyl ether, tetrahydrofuran, etc. at a temperature of −20° C. to 35° C. The thus-obtained organometallic compound (II) is reacted with an aldehyde of general formula (III) in a solvent such as benzene, toluene, xylene, etc. at a temperature of −10° C. to 15° C., and the reaction product is hydrolyzed under weakly acidic conditions produced by the presence of diluted hydrochloric acid, ammonium chloride or the like to give a trimethylcyclohexenyl compound of general formula (I).

The following examples are given to merely illustrate the invention in further detail and should by no means be construed as limiting the scope of the invention.

EXAMPLE 1

Synthesis of 1-(3-hydroxybutyryl)-2,4,4-trimethyl-2-cyclohexene

A solution of 18.6 g of N-methylaniline in 57 ml of benzene was added dropwise to a solution of Grignard reagent in diethylether, said Grignard reagent being prepared from 4.6 g of magnesium and 22.8 g of ethyl bromide, at a temperature of 0° C. to 5° C., and the mixture was stirred at 15° C. for 10 minutes. At the same temperature, a solution of 33.2 g of 1-acetyl-2,4,4-trimethyl-2-cyclohexene in 29 ml of benzene was added dropwise to the above-obtained solution. The mixture was stirred at room temperature for 30 minutes and then cooled to around −10° C. and a solution of 5.9 g of acetaldehyde in 14.3 ml of benzene was added dropwise thereto at a temperature of −13° C. to −10° C., followed by stirring at a temperature of −10° C. to −5° C. for 1 hour. To this mixture was added aqueous saturated ammonium chloride and the resulting mixture was extracted with three 100-ml portions of benzene. The benzene extract was washed with diluted hydrochloric acid and then washed thoroughly with water for neutralization and dried over anhydrous sodium sulfate. The benzene was removed from the extract using an evaporator and the residue was distilled under reduced pressure to give 17.8 g of a colorless to light-yellow liquid as the distillate fraction boiling at 85°–89° C./1–2 mm Hg. Based on the following analytical data, the product was identified as 1-(3-hydroxybutyryl)-2,4,4-trimethyl-2-cyclohexene.

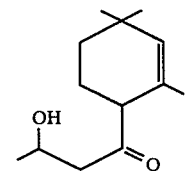

FD-Mass: m/e 210
IR (cm$^{-1}$): 3450, 2980, 2850, 1710, 1450, 1360
H$^1$-NMR ($\delta_{ppm}$ $^{CDCl_3}$): 0.92, 0.97 (each s, 6H,

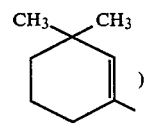
)

1.15 (d, 3H,

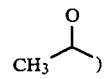
)

1.56 (s, 3H,

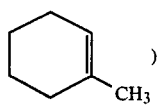
)

2.4–2.8 (m, 2H,

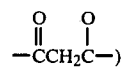
)

2.97 (t, 1H,

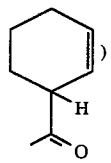
)

3.9–4.4 (m, 1H,

)

5.35 (s, 1H,

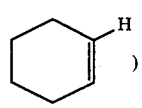
)

EXAMPLE 2

Synthesis of 1-(3-hydroxypentanoyl)-2,4,4-trimethyl-2-cyclohexene

The procedure of Example 1 was followed except that 7.8 g of propionaldehyde was used in lieu of 5.9 g of acetaldehyde, followed by distillation under reduced pressure to give 18.2 g of a colorless to light-yellow liquid as the distillate fraction boiling at 83°–98° C./0.5–2 mm Hg. Based on the following analytical data, the product was identified as 1-(3-hydroxypentanoyl)-2,4,4-trimethyl-2-cyclohexene.

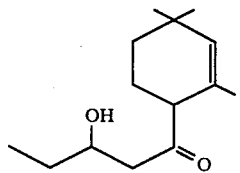

FD-Mass: m/e 224
IR (cm$^{-1}$): 3450, 2950, 2850, 1700, 1450, 1380, 1360
H$^1$-NMR ($\delta_{ppm}^{CDCl_3}$):
1.55 (s, 3H, 1.56 (s, 3H,

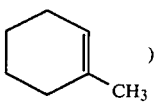
)

2.4–2.7 (m, 2H,

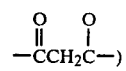
)

2.98 (t, 1H,

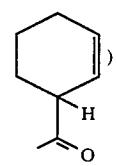
)

3.8–4.1 (m, 1H,

)

5.37 (s, 1H,

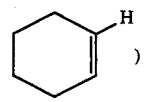
)

EXAMPLE 3

Synthesis of 1-(3-hydroxy-4-methylpentanoyl)-2,4,4-trimethyl-2-cyclohexene

The procedure of Example 1 was followed except that 9.6 g of isobutylaldehyde was used in lieu of 5.9 g of acetaldehyde, followed by distillation under reduced pressure to give 19.0 g of a colorless to light-yellow liquid as the distillate fraction boiling at 103°–108° C./0.5 mm Hg. Based on the following analytical data, the product was identified as 1-(3-hydroxy-4-methylpentanoyl)-2,4,4-trimethyl-2-cyclohexene.

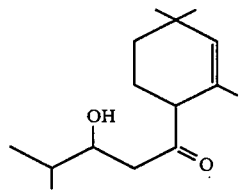

FD-Mass: m/e 238
IR (cm$^{-1}$): 3450, 2960, 2840, 1710, 1450, 1360
H$^1$-NMR ($\delta_{ppm}^{CCl_4}$):
1.53 (s, 3H, 2.35–2.50 (m, 2H, 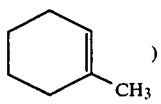

2.84 (t, 1H, 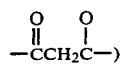

3.50–3.80 (m, 1H, 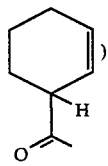

5.27 (s, 1H, 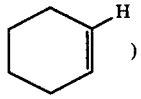

EXAMPLE 4

Perfume Composition of the Rose Type

A perfume composition having a rose-like note was prepared according to the following formula.

|  | Parts by weight |
|---|---|
| Phenylethyl alcohol | 300 |
| Geraniol | 150 |
| Citronellol | 150 |
| Linalool | 60 |
| Guaiac wood oil | 40 |
| Eugenol | 10 |
| Benzyl acetate | 70 |
| Phenylacetaldehyde | 5 |
| Citronellyl formate | 3 |
| Geranyl acetate | 10 |
| Cinnamic alcohol | 50 |
| Geranium oil | 30 |
| Aldehyde C-11 (*10% solution in DEP) | 1 |
| Aldehyde C-10 (*10% solution in DEP) | 1 |
| Nerolidol | 30 |
| Rose absolute | 10 |
| 1-(3-Hydroxybutyryl)-2,4,4-tri-methyl-2-cyclohexene | 80 |
|  | 1000 |

*DEP stands for diethyl phthalate.

The use of 80 parts by weight of 1-(3-hydroxypentanoyl)-2,4,4-trimethyl-2-cyclohexene or 1-(3-hydroxy-4-methylpentanoyl)-2,4,4-trimethyl-2-cyclohexene in place of 80 parts by weight of 1-(3-hydroxybutyryl)-2,4,4-trimethyl-2-cyclohexene in the above formula also gave a perfume composition having a rose-like note.

EXAMPLE 5

Perfume Composition of the Lilac Type

A perfume composition having a lilac-like note was prepared according to the following formula.

|  | Parts by weight |
|---|---|
| Terpineol | 150 |
| Hydroxycitronellal | 120 |
| Phenylethyl alcohol | 130 |
| Heliotropin | 80 |
| Cinnamic alcohol | 50 |
| Nerol | 20 |
| Vanillon | 20 |
| Linalool | 80 |
| Geraniol | 30 |
| Benzyl acetate | 50 |
| Anisaldehyde | 40 |
| Ylang-ylang oil | 60 |
| Isoeugenol | 20 |
| Styrax oil | 10 |
| Petitgrain oil | 10 |
| Hydrocinnamic aldehyde | 5 |
| Jasmin absolute | 5 |
| Aldehyde C-10 (*10% solution in DEP) | 5 |
| Farnesol | 30 |
| Indole (*10% solution in DEP) | 5 |
| 1-(3-Hydroxybutyryl)-2,4,4-trimethyl-2-cyclohexene | 80 |
|  | 1000 |

*DEP stands for diethyl phthalate.

The use of 80 parts by weight of 1-(3-hydroxypentanoyl)-2,4,4-trimethyl-2-cyclohexene or 1-(3-hydroxy-4-methylpentanoyl)-2,4,4-trimethyl-2-cyclohexene in place of 80 parts by weight of 1-(3-hydroxybutyryl)-2,4,4-trimethyl-2-cyclohexene in the above formula also gave a perfume composition having a lilac-like note.

EXAMPLE 6

Perfume Composition of the Violet Type

A perfume composition having a violet-like note was prepared according to the following formula.

|  | Parts by weight |
|---|---|
| α-Ionone | 300 |
| Methylionone | 30 |
| Benzyl acetate | 80 |
| Phenylethyl alcohol | 150 |
| Linalool | 30 |
| Geraniol | 30 |
| Ylang-ylang oil | 50 |
| Violet leaf oil | 5 |
| Vetiver oil | 20 |
| Sandalwood oil | 30 |
| Labdanum oil | 5 |
| Hydroxycitronellal | 50 |
| Heliotropin | 30 |
| Linalyl acetate | 40 |
| Musk ambrette | 20 |
| Jasmin absolute | 50 |
| 1-(3-Hydroxybutyryl)-2,4,4-trimethyl-2-cyclohexene | 80 |
|  | 1000 |

The use of 80 parts by weight of 1-(3-hydroxypentanoyl)-2,4,4-trimethyl-2-cyclohexene or 1-(3-hydroxy-4-methylpentanoyl)-2,4,4-trimethyl-2-cyclohexene in place of 80 parts by weight of 1-(3-hydroxybutyryl)-2,4,4-trimethyl-2-cyclohexene in the above formula also gave a perfume composition having a violet-like note.

EXAMPLE 7

Perfume Composition of the Jasmin Type

A perfume composition (base) having a jasmin-like note was prepared according to the following formula.

|  | Parts by weight |
|---|---|
| Benzyl acetate | 30 |
| Hexylcinnamic alcohol | 20 |
| Ylang-ylang oil | 5 |
| Phenylethyl alcohol | 8 |
| Linalool | 5 |
| Methylionone | 5 |
| Jasmin absolute | 3 |
| Hydroxycitronellal | 8 |
| Linalyl acetate | 3 |
| Nerol | 2 |
| Cinnamic alcohol | 3 |
| Indole | 1 |
| Musk ambrette | 2 |
| 1-(3-Hydroxybutyryl)-2,4,4-trimethyl-2-cyclohexene | 5 |
|  | 100 |

The use of 5 parts by weight of 1-(3-hydroxypentanoyl)-2,4,4-trimethyl-2-cyclohexene or 1-(3-hydroxy-4-methylpentanoyl)-2,4,4-trimethyl-2-cyclohexene in place of 5 parts by weight of 1-(3-hydroxybutyryl)-2,4,4-trimethyl-2-cyclohexene in the above formula also gave a perfume composition having a jasmin-like note.

EXAMPLE 8

Perfume Composition of the Muguet Type

A perfume composition (base) having a muguet-like note was prepared according to the following formula.

|  | Parts by weight |
|---|---|
| Hydroxycitronellal | 35 |
| Linalool | 10 |
| α-Terpineol | 10 |
| Phenylethyl alcohol | 5 |
| Ylang-ylang oil | 5 |
| Bergamot oil | 3 |
| Citronellol | 8 |
| Benzyl salicylate | 5 |
| Heliotropin | 3 |
| Coumarin | 3 |
| Musk tinc. | 5 |
| 1-(3-Hydroxybutyryl)-2,4,4-trimethyl-2-cyclohexene | 8 |
|  | 100 |

The use of 8 parts by weight of 1-(3-hydroxypentanoyl)-2,4,4-trimethyl-2-cyclohexene or 1-(3-hydroxy-4-methylpentanoyl)-2,4,4-trimethyl-2-cyclohexene in place of 8 parts by weight of 1-(3-hydroxybutyryl)-2,4,4-trimethyl-2-cyclohexene in the above formula also gave a perfume composition having a muguet-like note.

EXAMPLE 9

"Tutti-Frutti" Flavoring Composition

A "Tutti-Frutti" flavoring composition for food use was prepared according to the following formula.

|  | Parts by weight |
|---|---|
| Vanillin | 20 |
| Allyl caproate | 10 |
| Citral | 20 |
| Amyl butyrate | 35 |
| Orange oil | 45 |
| Ethyl butyrate | 75 |
| Ethyl acetate | 185 |
| Amyl acetate | 185 |
| Lemon oil | 415 |
| 1-(3-Hydroxybutyryl)-2,4,4-trimethyl-2-cyclohexene | 10 |
|  | 1000 |

The use of 10 parts by weight of 1-(3-hydroxypentanoyl)-2,4,4-trimethyl-2-cyclohexene or 1-(3-hydroxy-4-methylpentanoyl)-2,4,4-trimethyl-2-cyclohexene in place of 10 parts by weight of 1-(3-hydroxybutyryl)-2,4,4-trimethyl-2-cyclohexene in the above formula also gave a "Tutti-Frutti" flavoring composition for food use.

What is claimed is:

1. A trimethylcyclohexenyl compound of the general formula

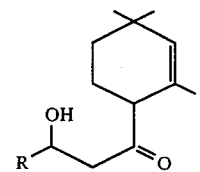

wherein R is a lower alkyl group.

2. The trimethylcyclohexenyl compound of claim 1, which is 1-(3-hydroxybutyryl)-2,4,4-trimethyl-2-cyclohexene.

3. The trimethylcyclohexenyl compound of claim 1, which is 1-(3-hydroxypentanoyl)-2,4,4-trimethyl-2-cyclohexene.

4. The trimethylcyclohexenyl compound of claim 1, which is 1-(3-hydroxy-4-methylpentanoyl)-2,4,4-trimethyl-2-cyclohexene.

5. An aroma composition which contains an olfactorily sensible amount of a trimethylcyclohexenyl compound of the general formula

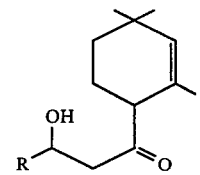

wherein R is a lower alkyl group.

6. A perfume, fragrance composition which contains an olfactorily sensible amount of a trimethylcyclohexenyl compound of the general formula

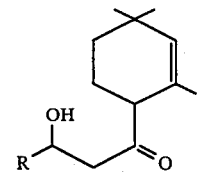

wherein R is a lower alkyl group.

7. The composition of claims 5 and 6, wherein the trimethylcyclohexenyl compound is 1-(3-hydroxybutyryl)-2,4,4-trimethyl-2-cyclohexene.

8. The composition of claims 5 and 6, wherein the trimethylcyclohexenyl compound is 1-(3-hydroxypentanoyl)-2,4,4-trimethyl-2-cyclohexene.

9. The composition of claims 5 and 6, wherein the trimethylcyclohexenyl compound is 1-(3-hydroxy-4-methylpentanoyl)-2,4,4-trimethyl-2-cyclohexene.

* * * * *